United States Patent
Westphal et al.

(10) Patent No.: US 9,599,558 B2
(45) Date of Patent: Mar. 21, 2017

(54) MEASURING DEVICE FOR MEASURING A MEASUREMENT OBJECT AND RELATED METHOD

(71) Applicant: Carl Zeiss Industrielle Messtechnik GmbH, Oberkochen (DE)

(72) Inventors: Peter Westphal, Jena (DE); Thomas Engel, Aalen (DE)

(73) Assignee: CARL ZEISS INDUSTRIELLE MESSTECHNIK GMBH, Oberkochen (DE)

( * ) Notice: Subject to any disclaimer, the term of this patent is extended or adjusted under 35 U.S.C. 154(b) by 465 days.

(21) Appl. No.: 13/961,583

(22) Filed: Aug. 7, 2013

(65) Prior Publication Data

US 2014/0043474 A1 Feb. 13, 2014

Related U.S. Application Data

(63) Continuation of application No. PCT/EP2012/074381, filed on Dec. 4, 2012, and a
(Continued)

(51) Int. Cl.
*H04N 7/18* (2006.01)
*G01N 21/55* (2014.01)
(Continued)

(52) U.S. Cl.
CPC ............. *G01N 21/55* (2013.01); *G01N 21/25* (2013.01); *G01N 21/21* (2013.01)

(58) Field of Classification Search
None
See application file for complete search history.

(56) References Cited

U.S. PATENT DOCUMENTS

| 4,924,079 A | 5/1990 | Opheij et al. |
| 5,878,152 A | 3/1999 | Sussman |

(Continued)

FOREIGN PATENT DOCUMENTS

| CN | 1043217 A | 6/1990 |
| DE | 2 158 228 A | 11/1985 |

(Continued)

OTHER PUBLICATIONS

Chromasens GmbH: truePIXa—An imaging system, measuring spectral reflectance; Apr. 2012; 8 pp.
(Continued)

*Primary Examiner* — Dakshesh Parikh
(74) *Attorney, Agent, or Firm* — Harness, Dickey & Pierce, P.L.C.

(57) ABSTRACT

A measuring device and corresponding method for measuring a measurement object, comprising an illumination device for illuminating the measurement object with an illumination pattern, a pattern generation device with at least one pattern generating element for bringing about a positionally variant intensity distribution of the illumination pattern, and an optical sensor arrangement for detecting the illumination pattern reflected and/or scattered by the measurement object. The measuring device has an optics which is telecentric at least on the measurement object side and is arranged in a beam path from the illumination device to the measurement object. The optical sensor arrangement detects the illumination pattern through at least one part of the telecentric optics. The pattern generating device is designed in such a way that the illumination pattern has a positionally and/or spectrally variant vertex focal length distribution on the measurement object side.

15 Claims, 11 Drawing Sheets

Related U.S. Application Data continuation-in-part of application No. PCT/EP2012/065477, filed on Aug. 7, 2012.

(60) Provisional application No. 61/733,110, filed on Dec. 4, 2012, provisional application No. 61/680,454, filed on Aug. 7, 2012.

(51) Int. Cl.
    *G01N 21/25*     (2006.01)
    *G01N 21/21*     (2006.01)

(56) References Cited

U.S. PATENT DOCUMENTS

| | | | |
|---|---|---|---|
| 5,880,846 A | 3/1999 | Hasman et al. | |
| 6,822,749 B1 | 11/2004 | Christoph | |
| 7,167,584 B2 | 1/2007 | Guern | |
| 2001/0045529 A1* | 11/2001 | Iketaki | G01J 3/4406 250/493.1 |
| 2006/0109483 A1* | 5/2006 | Marx | G01B 11/0608 356/609 |
| 2010/0145650 A1* | 6/2010 | Nahum | G01B 11/0608 702/97 |
| 2011/0080576 A1 | 4/2011 | Thiel et al. | |
| 2011/0122414 A1* | 5/2011 | Fleischer | G01B 9/02028 356/453 |
| 2011/0311132 A1* | 12/2011 | Meimoun | A61B 3/1015 382/162 |

FOREIGN PATENT DOCUMENTS

| | | |
|---|---|---|
| DE | 34 18 767 A1 | 11/1985 |
| DE | 198 16 270 A1 | 10/1999 |
| DE | 199 55 702 A1 | 5/2001 |
| DE | 103 40 803 A1 | 3/2005 |
| EP | 1 287 311 B1 | 4/2000 |
| FR | 2 748 322 | 11/1997 |
| WO | WO 01/51885 A1 | 7/2001 |
| WO | WO 2009/121922 A1 | 10/2009 |

OTHER PUBLICATIONS

Ronald A. Petrozzo et al.; Telecentric Lenses simply non contact metrology; Test & Measurement World XP-002694012; Oct. 2001; 4 pp.

International Search Report with Written Opinion of PCT/EP2012/065477; Mar. 8, 2013; 9 pp.

International Search Report with Written Opinion of PCT/EP2012/074381; Mar. 18, 2013; 11 pp.

English langauge translation of Chinese Office Action with Search Report for Chinese Application No. 201280075165.4; issued Aug. 1, 2016; 12 pp.

\* cited by examiner

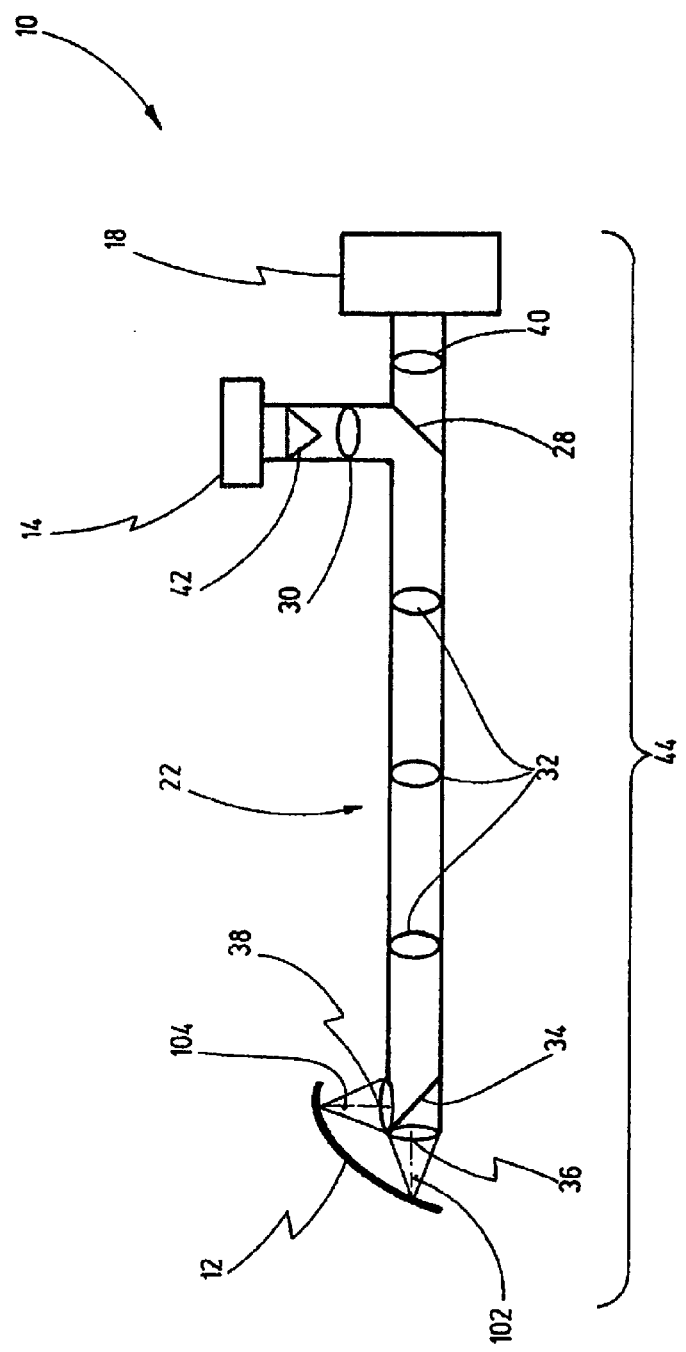

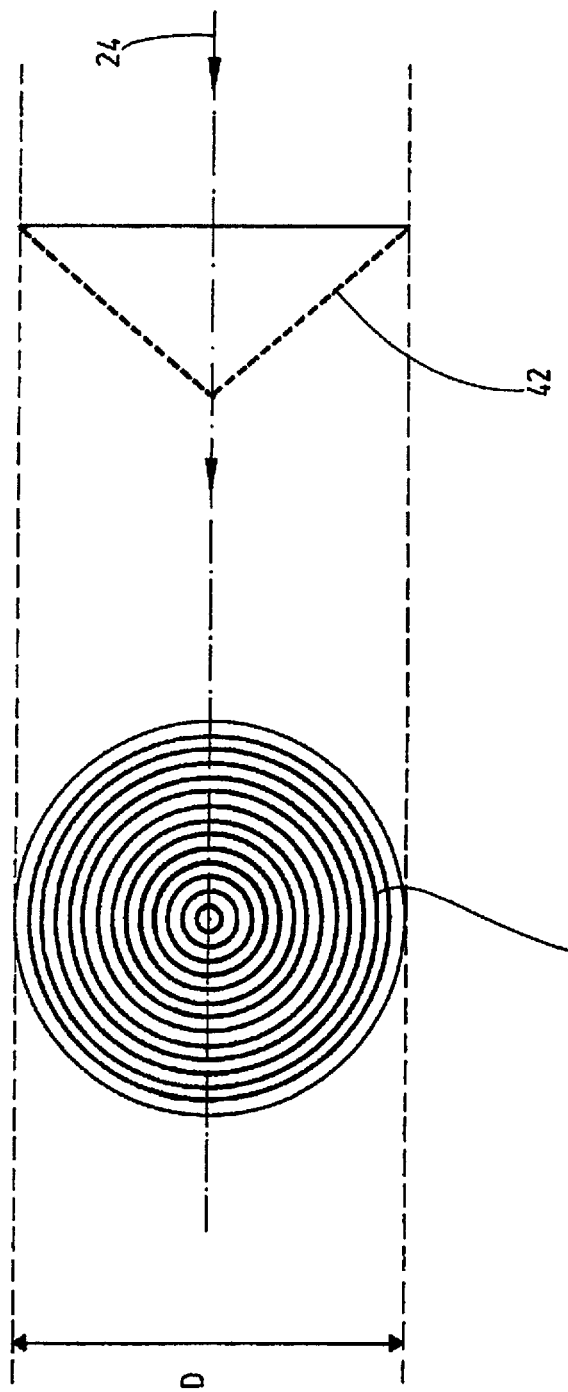

MEASURING DEVICE FOR MEASURING A MEASUREMENT OBJECT AND RELATED METHOD

CROSS-REFERENCE TO RELATED APPLICATIONS

This application is a continuation of International PCT application No. PCT/EP2012/074381, filed Dec. 4, 2012, and a continuation-in-part of International PCT application No. PCT/EP2012/065477, filed Aug. 7, 2012. This application also claims priority of U.S. provisional application No. 61/733,110, filed Dec. 4, 2012 and U.S. provisional application No. 61/680,454, filed on Aug. 7, 2012. The entire contents of these priority applications are incorporated herein by reference.

BACKGROUND OF THE INVENTION

The present invention relates to a measuring device for measuring a measurement object, comprising an illumination device for illuminating the measurement object with an illumination pattern, a pattern generation device with at least one pattern generating element for bringing about a positionally variant intensity distribution of the illumination pattern, and an optical sensor arrangement for detecting the illumination pattern reflected and/or scattered by the measurement object.

Furthermore, the present invention relates to an apparatus for measuring a measurement object comprising such a measuring device.

Furthermore, the present invention relates to a method for measuring a measurement object.

The present invention is generally concerned with contactless optical sensors for topologically detecting surfaces of measurement objects. The main areas of use for such sensors are industrial metrology, i.e. the metrological measurement of mechanical workpieces. In principle, however, sensors of this type can be used in all imaging operations.

One advantage of contactlessly measuring optical sensors of this type resides primarily in the fact that a surface can be measured significantly more rapidly in comparison with a sensor that effects tactile measurement.

Such measuring systems that effect tactile measurement are known in principle in the prior art. In this case, the surface topology to be measured is touched with the aid of a probe head or measuring probe. The measuring head has a touch element, e.g. a ruby sphere, and is part of a coordinate-measuring machine that brings the probe head with the touch element fixed therein in contact with the surface to be measured. The position and pressure force of the probe head or of the probe element is determined by means of strain gauges or other sensors. The surface contour is determined by punctiform or continuous tactile sensing. However, the speed of such systems that effect tactile measurement is limited. This arises, firstly, by virtue of the fact that a mechanical contact with the surface to be measured is always required and, secondly, the measurement effected is only ever a punctiform measurement. Although provision can indeed be made for automatically traversing a path on the surface in the context of a so-called "scanning process", even this is only a sequence of punctiform measurements. The size of the probe element additionally limits the measurable radii of the surface, i.e. small depressions generally cannot be detected. Furthermore, under certain circumstances, very hard probe elements can cause damage to very sensitive surfaces.

Furthermore, monochromatic confocal sensors have been proposed which focus monochromatic light, generally a laser beam, into the vicinity of the surface to be measured. The light reflected or scattered back from the surface to be measured is imaged onto a pinhole diaphragm in or in the vicinity of a confocal plane. The light power transmitted by the pinhole diaphragm is a measure of the distance between the object-side focal plane and the surface. By way of example, by keeping constant the transmitted light power, the surface can always be kept at the focus of the sensor. The surface topology can then be detected by point-by-point measurements along a predefined path in a manner similar to that in the case of a tactile sensor. Accordingly, the measurement here is also effected only in punctiform fashion and the requirements made of the control precision and the operating distance to be set are relatively precise.

Chromatic confocal sensors are also known in which a spectrally wide-band light is focused into the vicinity of the surface to be measured. The focusing is effected by means of an optics having a large longitudinal chromatic aberration, i.e. the focal plane varies greatly depending on the wavelength of the light. Likewise with the aid of a confocal pinhole diaphragm and a spectrometer, the distance between the sensor and the surface can be determined over a relatively large operating distance range, the length of which results from the difference between the object-side vertex focal length of the largest and smallest wavelengths of the wide-band light. Here, too, the measurement is, however, effected in each case only in punctiform fashion, as is shown for example in the document EP 1 287 311 B1.

Furthermore, so-called stripe illumination methods or deflectometry methods are known which usually project stripe patterns onto the surface to be measured. The surface topology to be measured deforms the stripes reflected by the surface. The reflected stripes are detected by means of a camera, i.e. a two-dimensional sensor array. The surface topology can be deduced from the measured deformation of the reflected stripe pattern. A simple variant of stripe illumination is laser line illumination, in which the form of a laser line radiated onto the measurement object is then evaluated in each case. Although a larger area can be detected and measured by this method, in return the measurement accuracy is lower than in the case of the punctiform measuring methods mentioned above. Furthermore, in the case of highly scattering surfaces, problems can occur on account of ambiguities in the evaluation.

Furthermore, interferometric methods are known in which the surface to be measured is irradiated with coherent or partly coherent light and is viewed in reflection. The surface topography then influences the light interference in terms of the depth, i.e. in the direction of propagation, or laterally, i.e. perpendicular to the direction of propagation. Interferometric methods with narrowband laser light are suitable for example for the high-precision measurement of lens surfaces. Spectrally wide-band light is used in the case of so-called white light interferometry or optical coherence tomography (OCT). The class of interferometric methods overall also includes holography. Consequently, all interferometric methods also require a reference beam path, which, however, always has a high sensitivity to disturbance in the measurement set-up.

Some of the methods mentioned above effect only punctiform measurement. The methods that effect areal measurement always operate with an angle between the illumination direction and viewing direction. However, in particular spatially greatly restricted applications which allow only limited viewing angles with respect to the surface to be measured, for example the measurement of bores or channels, do not allow large angles between the illumination direction and viewing direction, and so the precision of the methods that effect areal measurement thus also decreases.

Therefore, the document DE 199 55 702 A1 proposes an optical measuring method in which a luminous point or a ring is radiated as illumination pattern in the direction of the surface to be measured. Depending on whether the surface to be measured lies in the pattern, specific reflection figures arise, which can then be evaluated. From a possible distortion of the pattern, it is furthermore possible to determine not only the distance between the measuring point and the sensor but also an inclination of the probed surface point and thereby to deduce points lying around the measured point and their position.

Furthermore, the document DE 34 18 767 A1, for example, proposed using a specific aberration, the astigmatism, for the punctiform measurement of surface topographies.

Although the methods disclosed in the two documents mentioned above outline measuring systems in which the illumination direction and the viewing direction can run substantially parallel and coaxially with respect to one another, they yield a precise measurement only for a point respectively lying in the center of the respective sensor recording.

Therefore, it is an object of the present invention to provide a measuring device which eliminates the disadvantages of the methods mentioned above and enables a higher measurement speed in particular by means of a measurement that is not only punctiform.

SUMMARY OF THE INVENTION

In accordance with a first aspect of the invention it is therefore provided a measuring device for measuring a measurement object, comprising an illumination device for illuminating the measurement object with an illumination pattern, a pattern generation device with at least one pattern generating element for bringing about a positionally variant intensity distribution of the illumination pattern, and an optical sensor arrangement for detecting the illumination pattern reflected and/or scattered by the measurement object, wherein the measuring device furthermore has an optics which is telecentric at least on the measurement object side and which is arranged in a beam path from the illumination device to the measurement object, wherein the optical sensor arrangement is arranged in such a way that it detects the illumination pattern through at least one part of the telecentric optics, and wherein the pattern generating device with the at least one pattern generating element is designed in such a way that the illumination pattern has a positionally and/or spectrally variant vertex focal length distribution on the measurement object side.

The solution proposed in accordance with the first aspect thus illuminates the measurement object with an illumination pattern that is extended laterally, i.e. perpendicular to a direction of propagation of the light. The optical sensor arrangement is, in particular, an areal two-dimensional camera that detects the reflected and/or scattered illumination pattern. This is then followed by an evaluation of the imaging sharpness of the pattern, which is made possible by the positionally, or locationally, and/or spectrally variant vertex focal length distribution of the illumination pattern.

In other words, therefore, the illumination pattern now has a three-dimensional patterning provided on the one hand, by the lateral spatially variant intensity distribution. By way of example, the illumination pattern can be a multitude of concentric rings, a checkered pattern, a stripe pattern, etc. The illumination pattern furthermore has, on the other hand, a "third dimension". That is to say that a further coding is impressed on the illumination pattern in the third dimension, which further coding can be gathered on the basis of the image detected by means of the optical sensor arrangement. This is the positionally and/or spectrally variant vertex focal length distribution. A positionally variant vertex focal length distribution, as used herein and in the claims, means that the focal point can vary for every lateral position of the illumination pattern. By way of example, different rings or different boxes of a checkered pattern can have different depths of focus. Depending on which regions of the illumination pattern are finally imaged sharply, the position of the sharply imaged points can also be inferred and, furthermore, the position of the points situated between sharply imaged points can possibly even be inferred from a measure of the unsharpness.

At the same time, a spectrally variant vertex focal length distribution can also be present for every position of the illumination pattern. Basically, a longitudinal chromatic aberration is brought about in this case for each point of the pattern. Consequently, as in the case of a confocal chromatic sensor, for example, for each point of the illumination pattern a chromatic intensity distribution can be analyzed and the position of the point can be detected.

A "spectral variance" thus describes a wavelength dependence. A "positional variance" thus describes a dependence on a lateral position.

In accordance with a second aspect of the invention it is therefore provided an apparatus for measuring a measurement object comprising a measuring device for measuring a measurement object, comprising an illumination device for illuminating the measurement object with an illumination pattern, a pattern generation device with at least one pattern generating element for bringing about a positionally variant intensity distribution of the illumination pattern, and an optical sensor arrangement for detecting the illumination pattern reflected and/or scattered by the measurement object, wherein the measuring device furthermore has an optics which is telecentric at least on the measurement object side and which is arranged in a beam path from the illumination device to the measurement object, wherein the optical sensor arrangement is arranged in such a way that it detects the illumination pattern through at least one part of the telecentric optics, wherein the pattern generating device with the at least one pattern generating element is designed in such a way that the illumination pattern has a positionally and/or spectrally variant vertex focal length distribution on the measurement object side, and wherein the apparatus furthermore has at least one evaluation unit for evaluating an image detected by means of the optical sensor arrangement.

The method in accordance with the third aspect of the invention comprises the steps of illuminating the measurement object with an illumination pattern with positionally variant intensity distribution, wherein the illumination pattern furthermore has a positionally and/or spectrally variant vertex focal length on the measurement object side, detecting the illumination pattern reflected and/or scattered by the measurement object by means of an optical sensor arrangement, and evaluating an image sharpness and/or a spectral distribution over the entire detected illumination pattern.

The at least object-side telecentricity of the optics furthermore has the effect that an imaging scale of the measurement object is independent of its relative position with respect to the measuring device. Consequently, altered magnification ratios do not have to be taken into account in the evaluation, which simplifies the evaluation and thus additionally accelerates the measurement or improves the metrological accuracy.

In this case, the "vertex focal length" denotes the distance between the point of intersection of the light rays passing through a specific point of the illumination pattern and a surface of that optical element of the measuring device which is located the furthest on the measurement object side.

In accordance with a fourth aspect of the invention it is therefore provided an apparatus for measuring a measurement object comprising a measuring device for measuring a measurement object, comprising an illumination device for illuminating the measurement object with an illumination pattern, a pattern generation device with at least one pattern generating element for bringing about a positionally variant intensity distribution of the illumination pattern, and an optical sensor arrangement for detecting the illumination pattern reflected and/or scattered by the measurement object, wherein the measuring device furthermore has an optics which is telecentric at least on the measurement object side and which is arranged in a beam path from the illumination device to the measurement object, wherein the optical sensor arrangement is arranged in such a way that it detects the illumination pattern through at least one part of the telecentric optics, wherein the pattern generating device with the at least one pattern generating element is designed in such a way that the illumination pattern has a positionally and/or spectrally variant vertex focal length distribution on the measurement object side, wherein the measuring device furthermore has a further illumination device for illuminating the measurement object with a further illumination pattern, a further pattern generating device with at least one pattern generating element for bringing about a positionally variant intensity distribution of the further illumination pattern, a further optics which is telecentric at least on the measurement object side and which is arranged in a further beam path from the further illumination device to the measurement object, and a further optical sensor arrangement for detecting the illumination pattern reflected and/or scattered by the measurement object, wherein the further optical sensor arrangement is arranged in such a way that it detects the illumination pattern through at least one part of the further telecentric optics, and wherein the further pattern generating device with the at least one pattern generating element is designed in such a way that the further illumination pattern has a positionally and/or spectrally variant vertex focal length distribution on the measurement object side, and wherein the further optics has at least one beam deflecting element for expanding the further beam path via at least one circumferential arc section perpendicular to the beam path to the measurement object, and wherein the apparatus furthermore has at least one evaluation unit for evaluating an image detected by means of the optical sensor arrangement and/or the further optical sensor arrangement.

In one refinement of the measuring device it can be provided that the optical sensor arrangement is a camera, i.e. an areally or two-dimensionally measuring sensor, and wherein the pattern generating device with the at least one pattern generating element is designed in such a way that the illumination pattern has a positionally variant vertex focal length distribution on the measurement object side.

In this way it thus becomes possible to measure a large surface region with a single recording.

In a further refinement of the measuring device it can be provided that the optical sensor arrangement is a spectrometer or a spectrally resolving two-dimensional sensor, and wherein the pattern generating device with the at least one pattern generating element is designed in such a way that the illumination pattern has a spectrally variant vertex focal length distribution on the measurement object side.

In this refinement, too, areal detection of a large surface region of the measurement object to be measured can be accomplished by means of a single recording. In this case, the spectrometer can be, in particular, a multi-line spectrometer, as will be explained below. Moreover, the sensor can be a camera, in particular a digital camera, which detects a spectral resolution for each pixel. In this way, whole-area detection of a large surface region becomes possible even in the case of the refinement with a spectrally variant vertex focal length distribution.

In a further refinement of the measuring device it can be provided that a pattern generating element of the pattern generating device is a transmission structure extending at least partly obliquely with respect to the beam path of the radiation.

The transmission structure is thus arranged in the illumination beam path. The transmission structure generates the positionally variant intensity distribution and thus the illumination pattern. The illumination pattern is thus projected onto the measurement object by means of radiation through a transmission structure. If the transmission structure extends at least partly obliquely with respect to the beam path from the illumination device to the measurement object, a positional variance likewise arises for the focal position. Consequently, different focal positions can arise for different points of the transmission structure. As will be explained below, by way of example, a multitude of concentric rings can be provided, wherein each ring has a different focal position. Depending on the position of the surface, therefore, only a specific ring or a part of one or more rings is sharply imaged. Such an illumination pattern can be obtained for example by means of a cone as transmission structure.

A person of average skill in the art infers a direction of propagation of the "beam path" from the optical set-up of the arrangement. If the optics has refractive optical elements, then the direction of propagation of the beam path runs parallel to the optical axis of the refractive elements.

In a further refinement of the measuring device it can be provided that a first pattern generating element of the pattern generating device is a planar transmission structure extending perpendicular to the beam path, and wherein a second pattern generating element of the pattern generating device is a refractive optical element having a longitudinal chromatic aberration or an optical element having a spherical aberration.

The illumination pattern can likewise be generated with a transmission structure extending perpendicular to the beam path. A refractive optical element having a longitudinal chromatic aberration can furthermore bring about a spectrally variant vertex focal length for the entire illumination pattern. The measuring principle proposed can also be implemented by means of an optical element having a spherical aberration. The spherical aberration likewise causes the focal region to be stretched in the depth direction. Although a completely sharp imaging on the optical sensor arrangement is then effected in each case, that position in the depth direction parallel to the beam path at which the intensity of the reflected and/or scattered light is maximal can be found after corresponding calibration.

In a further refinement of the measuring device it can be provided that the measuring device furthermore has a first beam splitter in the optics, which first beam splitter splits the beam path into a first measurement beam path and into a second measurement beam path, wherein the first measurement beam path and the second measurement beam path are oriented perpendicular to one another.

In this way, as will be explained below, by way of example, a simultaneous measurement in two directions is made possible. By way of example, in this way, it is possible to determine the depth of a bore and at the same time to detect a distance to an edge of the bore.

In one refinement of the measuring device it can be provided that the first beam splitter is a dichroic beam splitter.

In this way, by way of example, the first measurement beam path can be operated with a first wavelength range and the second measurement beam path can be operated with a second wavelength range. In this way, a wavelength-dependent assignment to the first measurement beam path and the second measurement beam path can ultimately be effected during an evaluation. Even further simultaneously operable measurement beam paths can also be provided by means of further dichroic splitting of the beam path.

In a further refinement of the measuring device it can be provided that the first beam splitter is a polarization-optical beam splitter.

In this way, an assignment to the first and the second measurement beam path can be effected by means of two different polarizations, which enables an unambiguous evaluation.

In a further refinement of the measuring device it can be provided that the second pattern generating element of the pattern generating device is a refractive optical element having a longitudinal chromatic aberration, wherein the optics is designed in such a way that an intermediate image is generated in the optics, and wherein a chromatic graduated filter is arranged in a plane of the intermediate image.

A chromatic evaluation can be effected in this way. In particular, such an evaluation can be effected by means of a spectrometer and there is thus no need for a camera which carries out a spectral evaluation for each pixel. This can make possible a more expedient optical sensor arrangement, which makes it possible to provide an overall more expedient measuring device.

In a further refinement of the measuring device it can be provided that the illumination pattern generated by the pattern generating device is a grid-shaped point pattern, wherein a hole pattern arrangement is arranged between the optics and the optical sensor arrangement, wherein each hole of the hole pattern arrangement is connected to the optical sensor arrangement by means of an optical waveguide.

In particular, it can be provided in this case that the optical sensor arrangement is a multi-line spectrometer.

This refinement, too, enables a chromatic evaluation without the use of a relatively cost-intensive camera with spectral analysis for each pixel. Each hole of the hole pattern arrangement or of a so-called "pinhole array" can be assigned to a line of a multi-line spectrometer by means of an optical waveguide. In this way, each point of the pinhole array can be evaluated individually.

In a further refinement of the measuring device it can be provided that a housing having a housing section extending in elongate fashion is provided, wherein the optics has a relay optics in the housing section extending in elongate fashion, and wherein the beam path from the illumination device to the measurement object and a detection beam path from the measurement object to the optical sensor arrangement run parallel to one another through the relay optics.

This likewise affords the possibility of employing illumination and observation beam paths that run parallel and coaxially. In particular, this makes it possible to examine bores or surfaces situated in spatially very narrow or recessed environments.

In a further refinement of the measuring device it can be provided that the measuring device furthermore has a further illumination device for illuminating the measurement object with a further illumination pattern, a further pattern generating device with at least one pattern generating element for bringing about a positionally variant intensity distribution of the further illumination pattern, a further optics which is telecentric at least on the measurement object side and which is arranged in a further beam path from the further illumination device to the measurement object, and a further optical sensor arrangement for detecting the illumination pattern reflected and/or scattered by the measurement object, wherein the further optical sensor arrangement is arranged in such a way that it detects the illumination pattern through at least one part of the further telecentric optics, and wherein the further pattern generating device with the at least one pattern generating element is designed in such a way that the further illumination pattern has a positionally and/or spectrally variant vertex focal length distribution on the measurement object side, and wherein the further optics has at least one beam deflecting element for expanding the further beam path via at least one circumferential arc section perpendicular to the beam path to the measurement object.

A further independent, but identically acting sensor set-up is thus additionally provided in this way. An illumination pattern altered by this sensor set-up can be different from the illumination pattern of the other sensor set-up, but it can also be an identical illumination pattern.

In this way, too, measurement is thus enabled in two mutually perpendicular directions, for example a measurement in the depth direction of a bore and a measurement perpendicular thereto that monitors a distance to a bore edge. On account of the beam deflection via an initial arc section or possibly even via the entire circumference, however, it is not necessary to rotate the measuring device during measurement. Rather, a large circumferential arc section is measured simultaneously. In particular, the circumferential arc section can be 180°.

It goes without saying that the features mentioned above and those yet to be explained below can be used not only in the combination respectively specified, but also in other combinations or by themselves, without departing from the scope of the present invention.

BRIEF DESCRIPTION OF THE OF THE DRAWINGS

Embodiments of the invention are illustrated in the drawing and are explained in greater detail in the description below. In the figures:

FIG. 2 shows a schematic illustration of a further embodiment of a measuring device;

FIG. 3 shows an exemplary illustration of an illumination pattern;

Figure 4A:
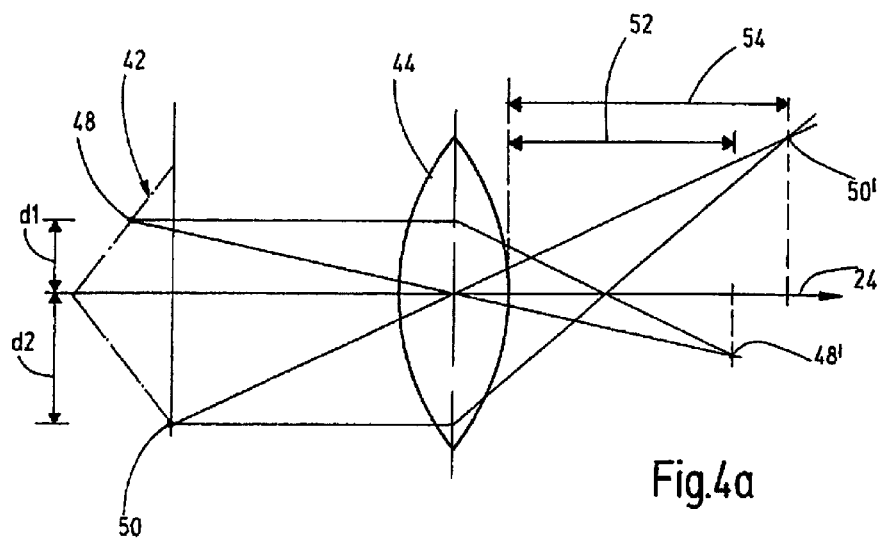
Figure 4B:
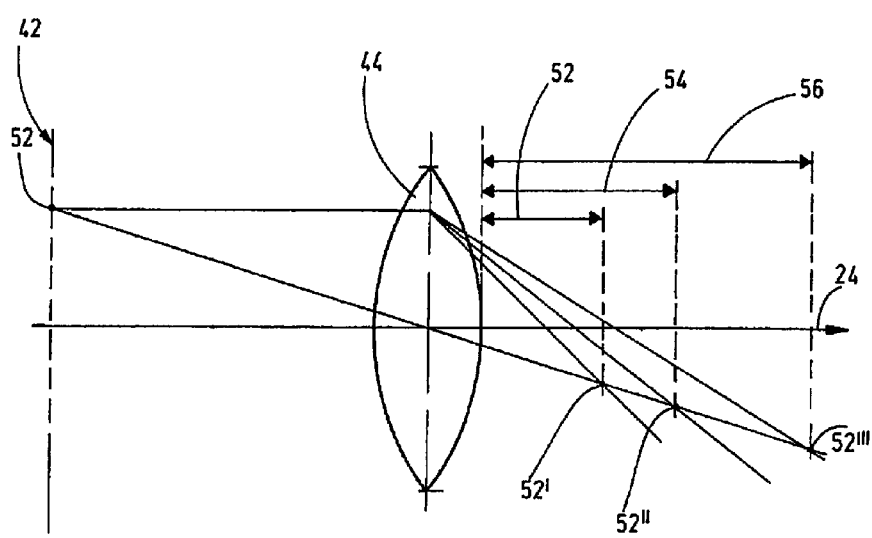
Figure 5:
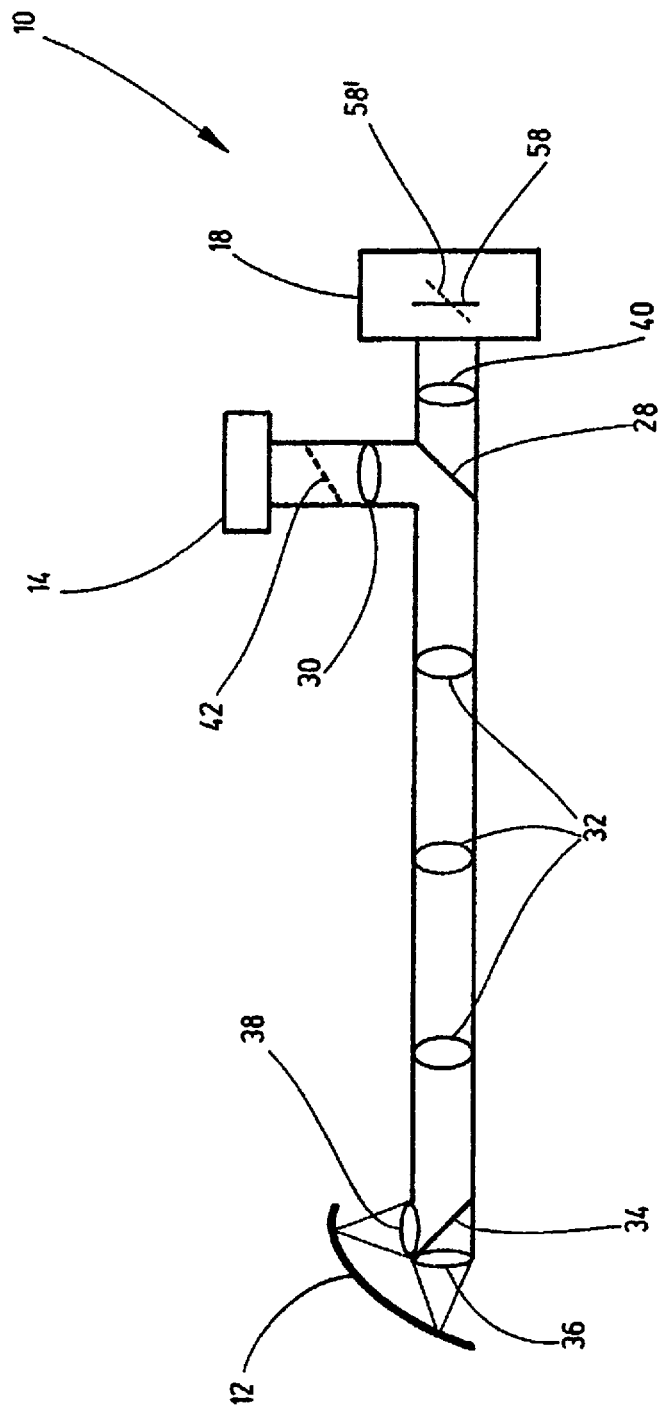
Figure 6:
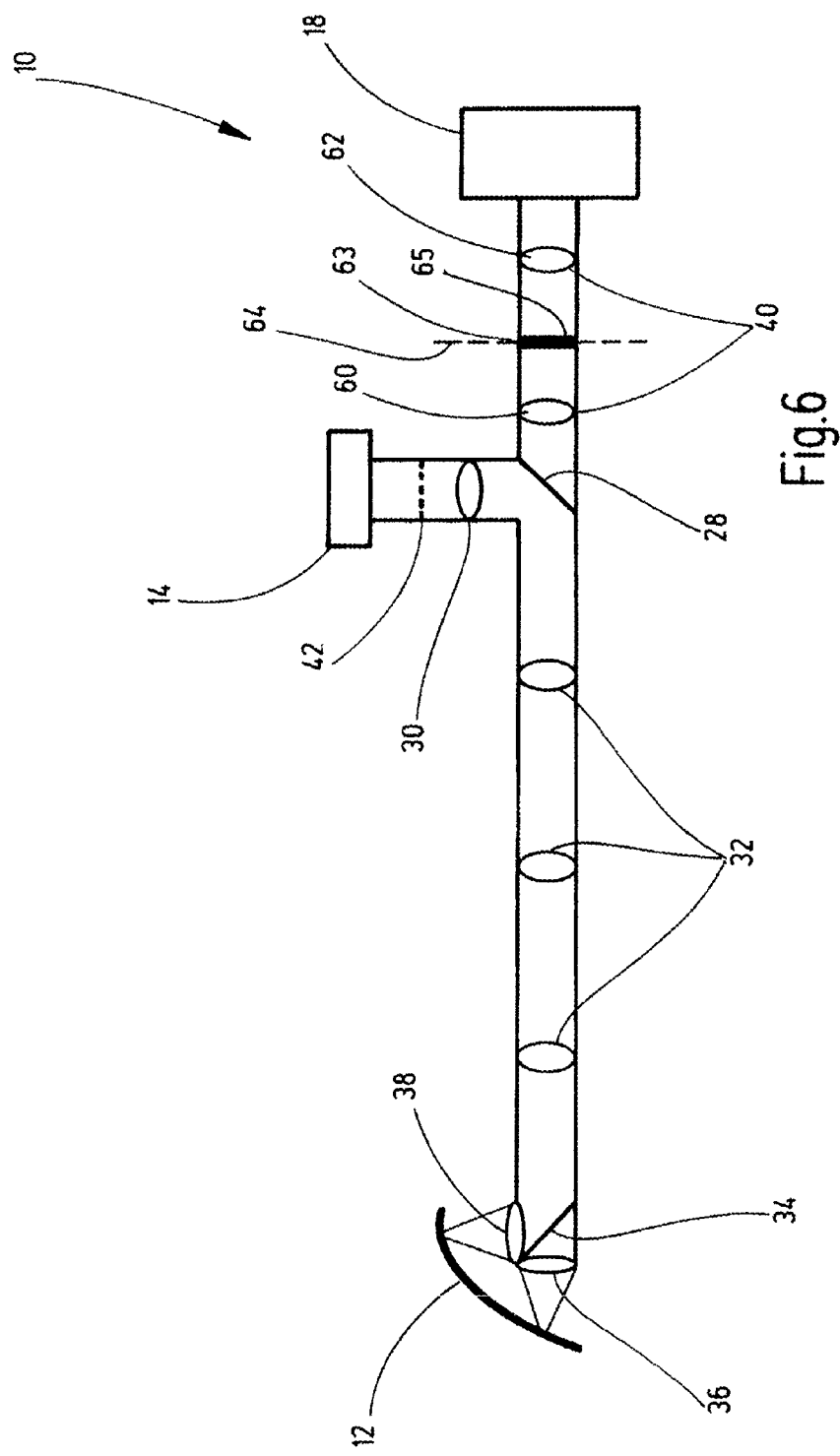
Figure 7:
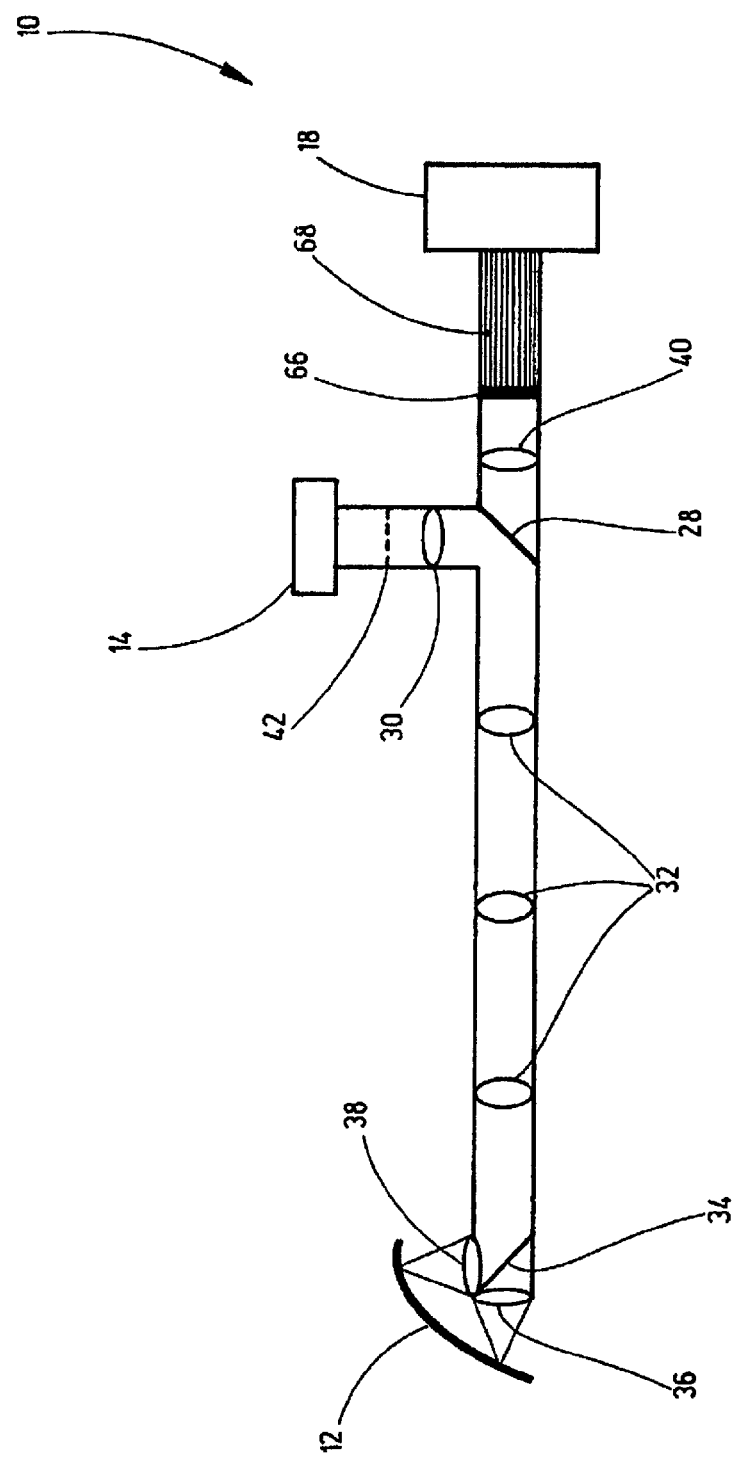
Figure 8:
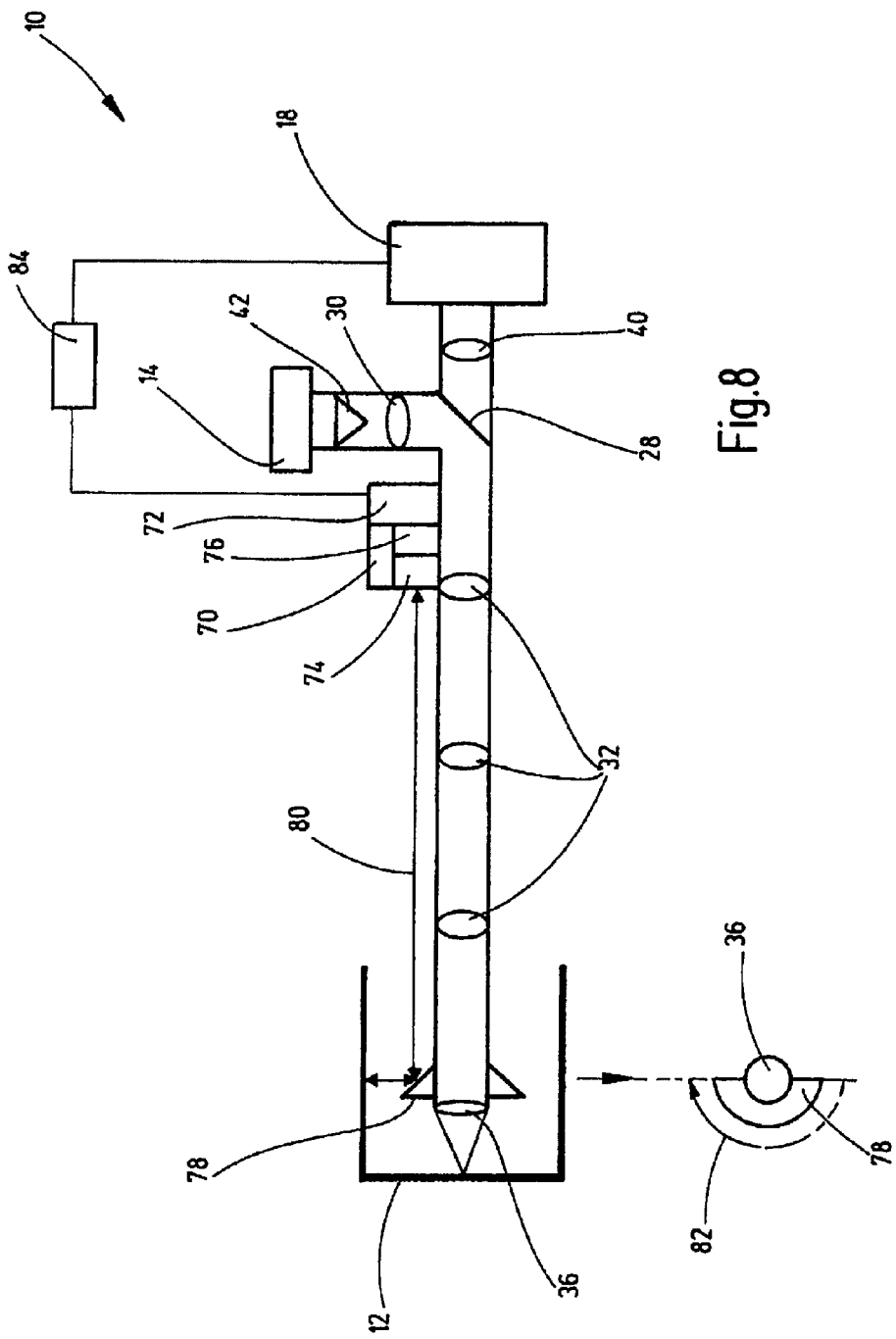
Figure 9:
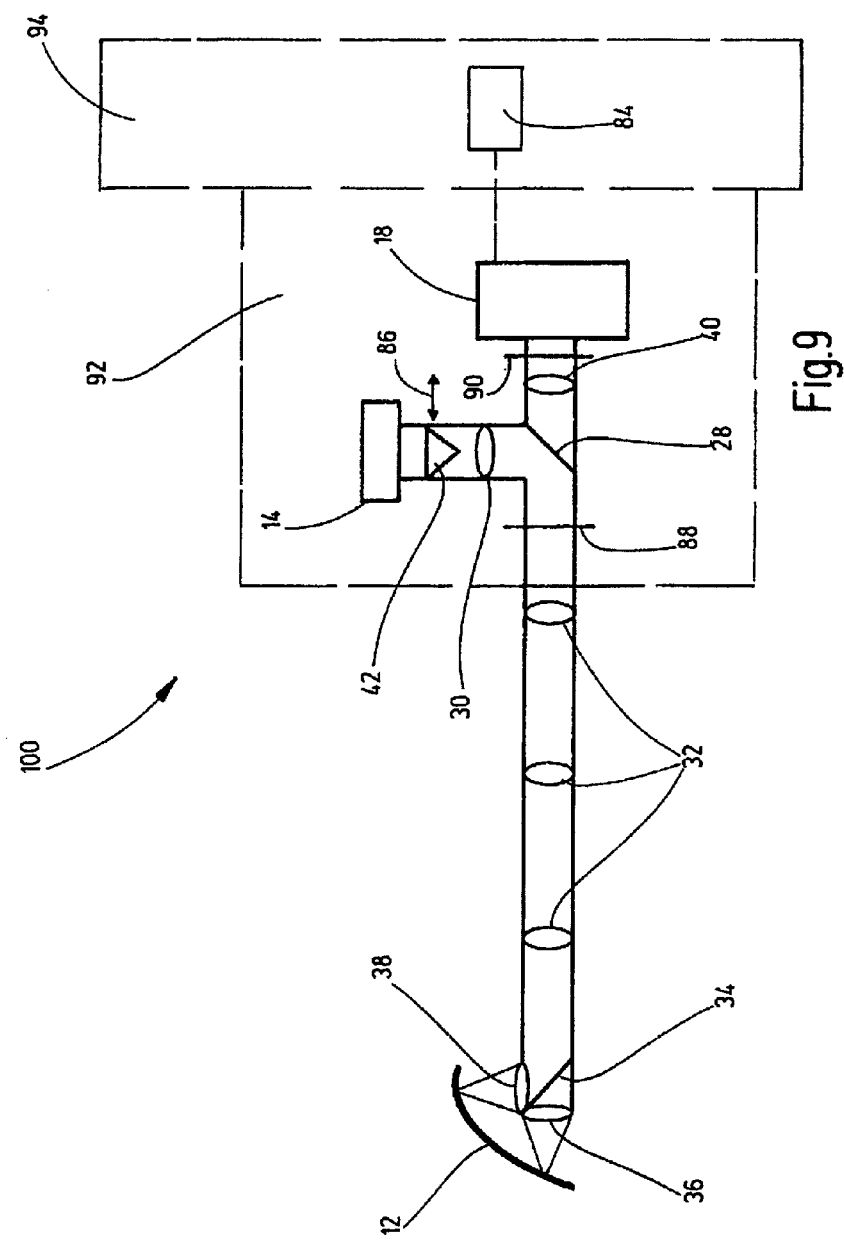
Figure 10:
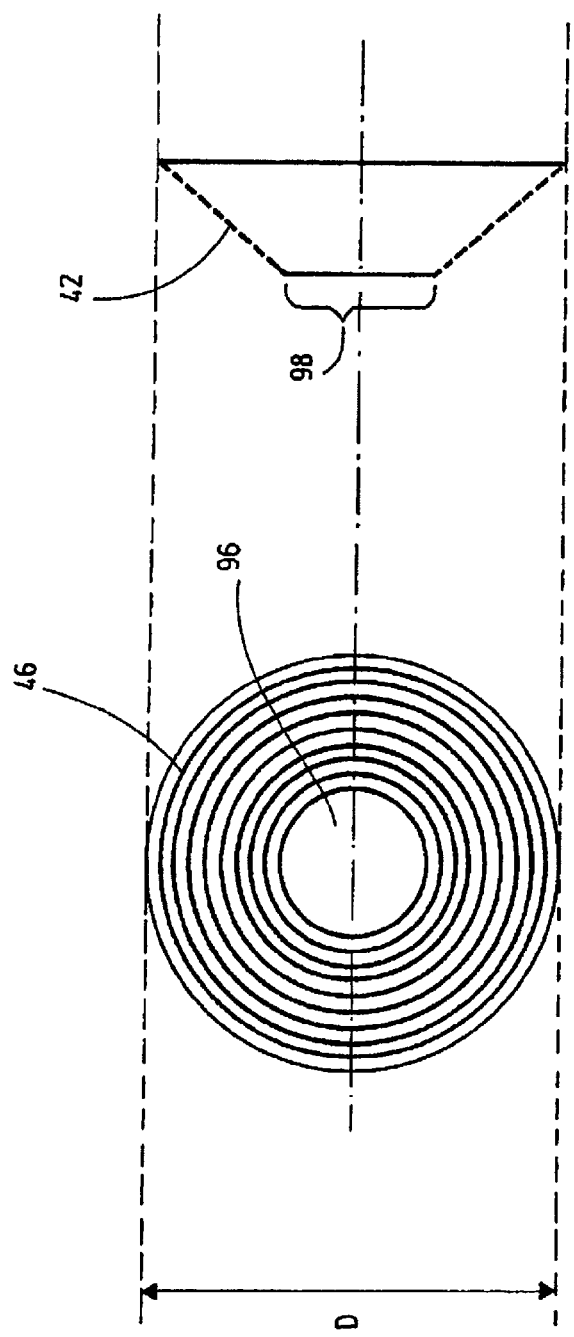

FIG. 4*a* shows a schematic illustration for elucidating the different vertex focal lengths in the case of an obliquely arranged transmission structure and a resultant positionally variant vertex focal length distribution;

FIG. 4*b* shows a schematic illustration for elucidating a spectrally variant vertex focal length distribution;

FIG. 5 shows a further embodiment of a measuring device;

FIG. 6 shows yet another embodiment of a measuring device;

FIG. 7 shows yet another embodiment of a measuring device;

FIG. 8 shows yet another embodiment of a measuring device;

FIG. 9 shows a schematic illustration of an embodiment of an apparatus;

FIG. 10 shows a further example of a possible illumination pattern; and

Figure 11:
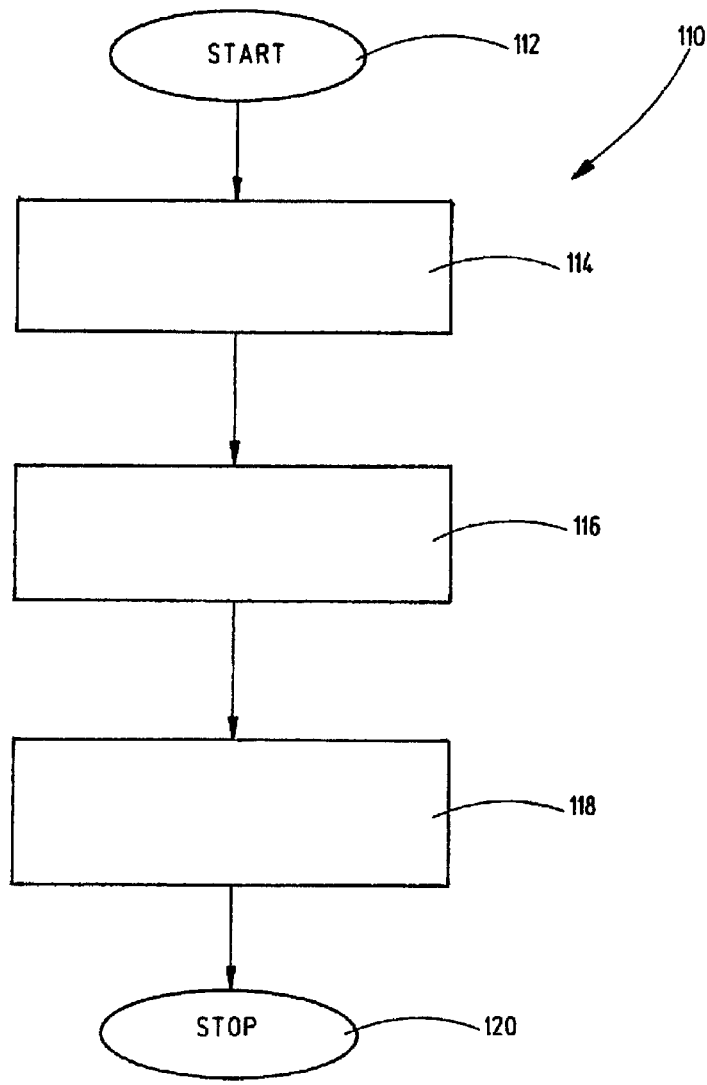

FIG. 11 shows a schematic flow chart of a method.

DETAILED DESCRIPTION OF THE PREFERRED EMBODIMENTS

Figure 1:
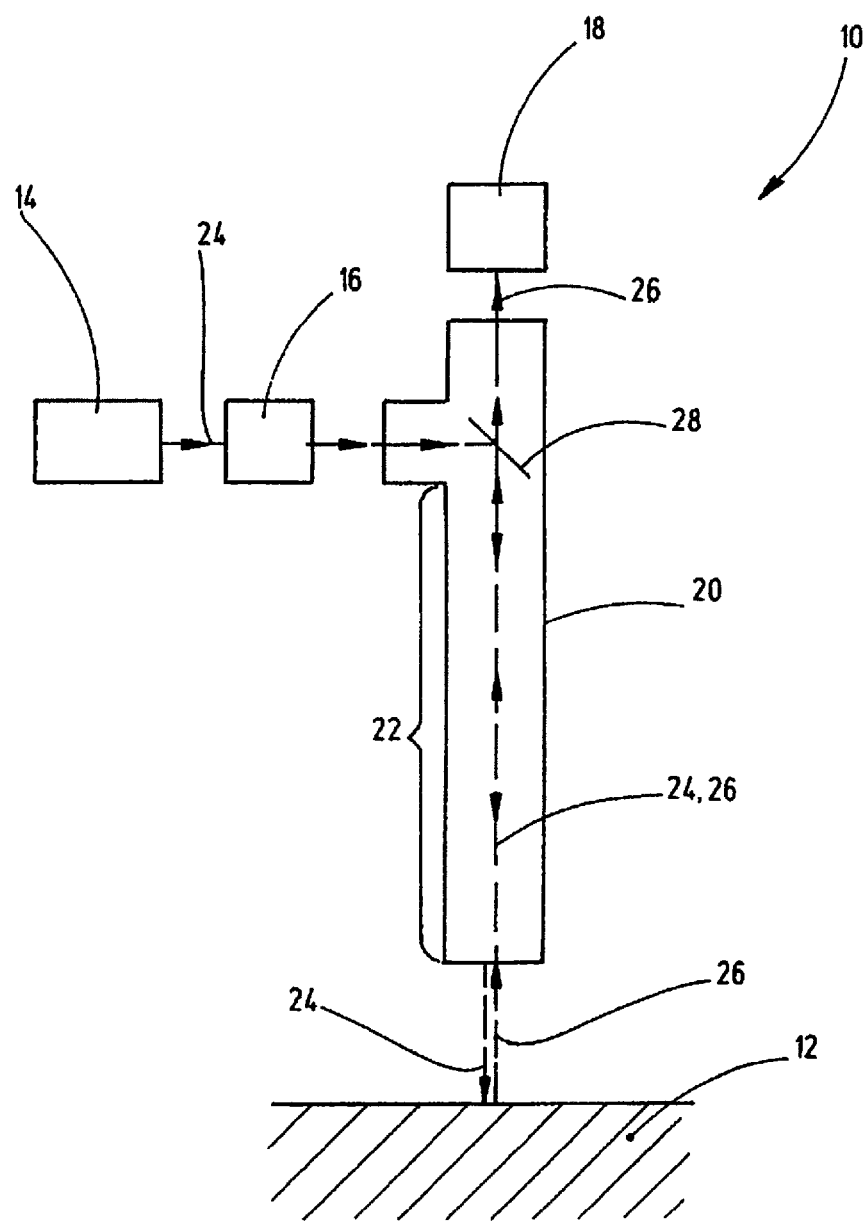
FIG. 1 shows a schematic illustration of a measuring device in accordance with a first aspect of the invention.

FIG. 1 shows a schematic illustration of a measuring device 10. The measuring device 10 serves for measuring a measurement object 12.

For this purpose, the measuring device 10 comprises an illumination device 14 and a pattern generating device 16. By means of the illumination device 14 and the pattern generating device 16, an illumination pattern is radiated onto the measurement object 12, wherein the light reflected and/or scattered by the measurement object 12 is detected by means of an optical sensor arrangement 18.

The measuring device 10 can comprise a housing 20 having a housing section 22 extending in elongate fashion, which housing section can be pushed for example into a region that otherwise is difficult to access in spatial terms, for example a bore. In principle, however, the spatial-physical configuration of the measuring device 10 is arbitrary.

A beam path 24 runs from the illumination device 14 to the measurement object 12. The light which is reflected and/or scattered by the measurement object 12 and is detected by means of the optical sensor arrangement 18 is represented by a beam path designated by 26. An illumination beam path 24 and a detection beam path 26 are present. These run parallel and coaxially with respect to one another in particular in the elongate housing section 22. The partly separate illustration of illumination beam path 24 and detection beam path 26 has been undertaken merely for illustration purposes.

An area region of the measurement object 12 is illuminated by means of the illumination device 14. The light reflected and/or scattered by said area region is detected by means of the optical sensor arrangement 18. The illumination beam path 24 and the detection beam path 26 are therefore separated from one another by means of a beam splitter 28. The arrangement of illumination device 14 and optical sensor arrangement 18 should be understood merely by way of example. They can also be interchanged, in principle.

In this case, the pattern generating device 16 is designed in such a way that an illumination pattern radiated from the illumination device 14 to the measurement object 12 has a positionally and/or spectrally variant vertex focal length distribution. The latter will be explained in even greater detail below. The image detected by the optical sensor arrangement 18 can therefore be examined with regard to a spectrally and/or positionally dependent image sharpness, from which it is possible to deduce a position of a correspondingly detected point on the measurement object relative to the measuring device 10.

FIG. 2 shows a schematically illustrated embodiment of the measuring device 10. Identical elements are identified by identical reference signs therein and will not be explained again below.

An illumination optical element 30 and a relay optics 32 consisting of a plurality of optical elements are illustrated schematically. In this case, the relay optics 32 extends in the elongate housing section 22. A further beam splitter 34 is provided in an end of the elongate housing section 22 that faces the measurement object 12, said further beam splitter splitting the illumination beam path 24 into a first measurement beam path 102 in a longitudinal direction and a second measurement beam path 104 in a transverse direction. Two area regions of the measurement object 12 can be measured in this way. The beam path scattered and/or reflected by the measurement object 12 runs through the beam splitter 34 and the beam splitter 28 and is imaged onto the optical sensor arrangement 18 by an imaging optical element 40. Furthermore, a transmission structure 42 is provided in the illumination beam path. In the embodiment illustrated, the transmission structure 42 is a conical grating. A positionally variant intensity distribution is achieved by means of the grating. In other words, there are lateral regions through which the light from the illumination device 14 can pass, and regions in which it is blocked. Furthermore, the regions in which the light passes through the transmission structure 42 lie at different depths on the illumination beam path 24.

This is illustrated schematically in FIG. 3. In this way, a multitude of concentric rings arise as illumination pattern 46. The ring having the largest diameter has the diameter D. In this case, each ring has a different depth position in the transmission structure 42 in the illumination direction. Consequently, the focal position of each ring during the projection is also different.

The first measurement beam path 102 and the second measurement beam path 104 can be situated at a right angle relative to one another. In principle, however, any other angle between the first measurement beam path 102 and the second measurement beam path 104 is also possible. The beam splitter 34 can be a dichroic element. The beam splitting then takes place by means of different wavelength ranges. However, a polarization beam splitter can also be involved. The beam splitting then takes place by means of different polarizations. The relay optics 32 can be embodied for example by means of a plurality of field lenses. However, the relay optics 32 can also have one or more GRIN (gradient-index) lenses. The relay optics 32 can also be implemented by means of an image-maintaining optical-fiber bundle. A combination of one or more of these configurations is also conceivable.

The arrangement of illumination device 14 and optical sensor arrangement 18 as illustrated in FIG. 2 can also be interchanged, in principle. Furthermore, even further dichroic beam splitters can be provided. By means of a cascading of a plurality of dichroic beam splitters, it is possible to provide even further measurement beam paths in addition to the measurement beam paths 102 and 104. By using a spectrally switchable radiation source 14, it is then possible to select the measurement beam path. A spectrally switchable radiation source 14 can be formed, for example, by means of a plurality of individually switchable LEDs having different centroid wavelengths or groups of LEDs having an identical centroid wavelength.

The grating cone arrangement illustrated in FIG. 3 serves as transmission structure. A structuring that is partly transparent and partly opaque is situated on the conically shaped surface of the transmission structure 42. The structuring can have, for example, concentric rings as illustrated in FIG. 3.

In principle, however, any other type of structuring can also be used, in particular a checkered, honeycomb-like or grating-like pattern. Hole structures, stripes or stochastic patterns are also conceivable. In particular, it is also possible to use periodic structures with different spatial frequencies. The transmission structure can also be subdivided in a segment-like manner, wherein each segment can have a different structuring. Furthermore, it is also possible to provide only a part of the available cross section with the structuring for bringing about the illumination pattern 46. From the illumination device 14, the transmission structure 42 is projected as illumination pattern 46 via the illumination optical element 30, the beam splitter 28, the relay optics 32 and the front optical element 36 or the transverse optical element 38 onto the measurement object 12. On account of the conical shape of the transmission structure 42, only specific parts of the transmission structure 42 are sharply projected onto the surface of the measurement object 12. The projected radiation reflected and/or scattered by the surface is imaged via the front optical element 36 or the transverse optical element 38 and also the relay optics 32, the beam splitter 28 and the imaging optical element 40 onto the optical sensor arrangement 18. The optical sensor arrangement 18 in FIG. 2 can be designed as a digital camera. The areal or two-dimensionally extending sensor chip of the camera is perpendicular here to an optical axis of the imaging optical element 40.

If the illumination pattern 46 consisting of concentric rings, as illustrated in FIG. 3, is assumed by way of example and it is furthermore supposed by way of example that the surface to be measured of the measurement object 12 is planar and, for example, perpendicular to the optical axis of the front optical element 36, in this case only a few rings or in an extreme case only one ring are/is sharply imaged by the optical sensor arrangement 18. Since a defined distance to, for example, the front optical element 36 can be assigned to each ring, it is possible—presupposing a corresponding distance calibration—to detect an optical distance of the surface of the measurement object. An optical distance sensor is thus available. If the surface of the measurement object 12 is not perpendicular to the optical axis of the front optical element 36 or if the latter is tilted, the sharply imaged rings become ellipses. Their position, i.e. the position of the two axes of the ellipse, and their shape, i.e. the eccentricity of the ellipse, provide information about the direction and the tilting angle of the surface of the measurement object. In the case of arbitrarily tilted or deformed surfaces of the measurement object 12, correspondingly more complex ring-like, but under certain circumstances no longer round or elliptical structures are obtained over the detection region of the optical sensor arrangement 18. The image detected by means of the optical sensor arrangement 18 is then sharp only at specific locations. In this case, it is necessary to carry out an image evaluation of position, shape and sharpness of the reflected and/or scattered ring structures in order to determine the surface topology.

In any case, however, there is obtained not just an evaluation with information from a point on the surface of the measurement object. The measuring device illustrated is able to determine, with one camera recording, topological information about an area region corresponding to the projection area. On account of the at least object-side telecentricity of an optics 44, no variation whatsoever of the magnification or of the imaging scale furthermore need be taken into account. For the illumination of the measurement object 12, the illumination optical element 30, the beam splitter 28, the relay optics 32 and the front optical element 36 or the transverse optical element 38 form the optics of the illumination beam path 24. For the "return path", they are the same elements apart from the illumination optical element 30, which is replaced by the imaging optical element 40.

In comparison with a pure point sensor, the advantage is thus afforded that far fewer positions of the surface to be measured of the measurement object 12 need be moved to, as a result of which the entire measurement process can take place significantly more rapidly. Furthermore, the advantage is afforded that the position of the measuring device relative to the surface of the measurement object 12 can already be detected with a single measurement, i.e. a single image. It is possible to predict how, in the case of an area to be measured which is larger than the projection area, the next measurement position should advantageously be chosen. An advantage of the greater speed is manifested, in particular, if only very few items of metric information about the measurement object 12 are present beforehand.

A second measurement beam path 104 via the transverse optical element 38 can be used to measure simultaneously or sequentially topological information at a different angle. In order to be able to unambiguously assign the measurement beam paths 102 and 104 of longitudinal and transverse sensors, the radiation is split spectrally or polarization-optically at the beam splitter 34. In this case, additionally on the sensor side, i.e. in the optical sensor arrangement 18, a corresponding assignment then has to be effected by selection, for example. In the case of spectral splitting, i.e. a design of the beam splitter 34 as a dichroic beam splitter, by way of example, the radiation source of the illumination device 14 can be a blue LED or a monochromatic light provided with a first wavelength can be provided for a longitudinal sensor, i.e. the beam path 102 through the front optical element 36. For the transverse sensor, i.e. the second measurement beam path 104 through the transverse optical element 38, by way of example, a green LED or a monochromatic light source having a second wavelength can be provided. If the beam splitter 34 is then designed as a dichroic beam splitter having a splitting or phase edge between the first wavelength and the second wavelength, for example between blue and green, the changeover between the use of the longitudinal sensor and the transverse sensor can be effected by changeover of the illumination by means of the illumination device 14 between blue and green, or between the first and second wavelengths. In this case, even a monochrome camera is suitable in the optical sensor arrangement 18. For a simultaneous measurement both by means of the longitudinal sensor and by means of the transverse sensor, a color camera would then be advantageous, wherein the color camera can also be a multichip camera. Of course, alongside LEDs (light-emitting diodes), it is also possible to use other radiation sources having arbitrary other first and second wavelengths as centroid wavelengths.

In the case of polarization-optical splitting, the beam splitter 34 splits the illumination radiation from the illumination device 14 into s- and p-polarized light, for example. On the detection side in the optical sensor arrangement 18, polarization-sensitive splitting optical units are then likewise provided (not illustrated in FIG. 2) in order to realize the assignment to longitudinal sensor and transverse sensor. In order to avoid movable elements, provision can be made for the optical sensor arrangement 18 to have a first areal camera and a second areal camera, onto which the s- and p-polarized light is respectively directed. Alternatively, the sensitive area, i.e. the sensor area of a single two-dimensional or areal camera can also be divided as in the case of the sensors. In principle, it is possible, alongside the two longitudinal and transverse sensors indicated schematically, by means of further beam splitters, also to supplement even further transverse sensors and further measurement beam paths with other viewing directions.

FIG. 3 shows the transmission structure 42 in detail. The transmission structure 42 illustrated in FIG. 3 is designed as a grating cone. The cone can, for example, be completely filled with glass or hollow on the inside. By way of example, a transmission structure composed of concentric rings is applied on the conically shaped surface of the cone, said transmission structure producing the illumination pattern 46 illustrated in FIG. 3. The dark rings stand for opaque regions, which can be produced for example by vapor deposition of chromium onto the surface of the transmission structure 42. The surface of the transmission structure 42 need not necessarily be conical; it can also have some other non-planar form, e.g. spherical or ellipsoidal. The curvature of the surface can face either in the direction of the illumination beam path 24 or in the opposite direction. It is also possible to provide a stepped plate with concentric rings, or else other types of structure. If the transmission structure 42 is filled, a prism effect occurs during the deflection of the illumination beam 24. A transmission structure 42 embedded on both sides can also be provided, that is to say that both the internal space of the cone and the complementary external space are completely filled, such that a plane-parallel plate is effectively produced. It is also possible to provide a prism having a separating location by means of the cone angle of the prism, in order to realize different measurement geometries.

FIG. 4a shows by way of example an illustration of the effect of the transmission structure 42 during the illumination of a measurement object 12. The illustration schematically shows an imaging of a first point 48 and of a second point 50 on the transmission structure 42. The imaging is effected by the optics 44, which is schematically illustrated on the basis of a single element. The illumination direction of the illumination beam path 24 is indicated schematically. The first point 48 is at a lateral distance d from an optical axis of the optics 44. This results in a ring having a radius d. The same correspondingly applies to the point 50, which is at a lateral distance d2, thus resulting in a ring having a radius d2. The beam paths are depicted schematically. As can be discerned, the rings are thus imaged sharply as points 48' and 50', respectively, also at different depths along the illumination beam path 24. The pattern of the first point 48 thus has a first vertex focal length 52 from the imaging optics 44. The pattern of the second point 50 has a second vertex focal length 54 from the imaging optics 44. The vertex focal lengths 52 and 54 are different. Depending on the depth at which the measurement object 12 is situated, a different ring is imaged sharply. By way of example, if the surface of the measurement object 12 is exactly at the level of the point 48 or at a distance from the imaging optics 44 which corresponds to the vertex focal length 52, the point 48 is correspondingly also detected sharply by the sensor arrangement 18 or a corresponding ring is sharply detected if an illumination pattern 46 as in FIG. 3 is used.

The illumination pattern 46 brought about by means of the transmission structure 42 correspondingly has a positionally variant vertex focal length distribution.

By contrast, FIG. 4b illustrates an example in which a spectrally variant vertex focal length distribution is provided. In this case, the transmission structure 42 is oriented perpendicular to the illumination beam path 24. The imaging optics 44 deliberately has a significant longitudinal chromatic aberration. The latter can be brought about, in particular, by the front optical element 36 and/or the transverse optical element 38 correspondingly being chosen as refractive optical elements having a dispersion behavior that leads to a high longitudinal chromatic aberration. A vertex focal length of an imaged point 52 of the transmission structure 42 is therefore wavelength-dependent and leads to a wavelength-dependent distortion of the focal point. FIG. 4b illustrates the focal point position 52', 52" and 52''' by way of example for three wavelengths. This leads to wavelength-dependent vertex focal lengths 52, 54 and 56 that differ from one another. By means of a wavelength-dependent evaluation, for example by means of a spectrometer or a camera in which each pixel of a sensor array makes possible a spectral evaluation, a depth position of a surface of the measurement object 12 can likewise be deduced. By way of example, if the surface of the measurement object 12 is at a distance from the optics 44 which corresponds exactly to the vertex focal length 54, the reflected and/or scattered light has a spectral intensity maximum at the corresponding associated wavelength. By means of a calibration, therefore, it is possible to obtain depth information for each pixel with respect to the entire projection region of the transmission structure 42.

It goes without saying that both "depth codings" of the illumination pattern 46 can also be combined, that is to say that both a positional variance of the vertex focal length 52, 54 and a spectral variance can be introduced.

FIG. 5 shows a further embodiment of the measuring device 10. Identical elements are identified by identical reference signs and will not be explained again below.

Instead of a cone grating as transmission structure 42, a planar, i.e. plane, tilted transmission structure 42, i.e. tilted with respect to the direction of propagation of an illumination beam path 24, is used for the illumination. A structuring of this transmission structure 42 can consist of parallel stripes, for example, but in principle any other type of structuring can also be used, in particular checkered, honeycomb- or grating-like patterns, hole structures and rings or stochastic patterns. In particular, periodic structures having different spatial frequencies can also be used.

In this embodiment of the measuring device 10, a sensor array or sensor chip 58 can be arranged both perpendicular to an optical axis of the imaging optical element 40 and in a manner tilted with respect thereto, as is identified by the position 58'. Furthermore, the functioning of this embodiment corresponds to the embodiment illustrated in FIG. 3.

FIG. 6 also shows a further embodiment of a measuring device 10. Identical elements are once again identified by identical reference signs and will not be explained again.

In this embodiment, the transmission structure 42 is once again planar and arranged perpendicular to an optical axis or direction of propagation of the illumination beam path 24. In order to obtain distance or depth information about the surface of the measurement object 12 for each position of an illumination pattern 46 in this case as well, the front optical element 36 and the transverse optical element 38 comprise optical elements having a large longitudinal chromatic aberration. A radiation source of the illumination device 14 is of wide-band design, e.g. in the form of white light LEDs or else multichromatic combinations of LEDs. Alternatively, it is also possible for example to configure the front optical element 36 and/or the transverse optical element 38 with other image aberrations, for example to provide a great image or object field curvature (spherical aberration), in order to be able to use plane transmission structures 42. In order to be able to carry out an evaluation by means of the optical sensor arrangement 18, the imaging optical element 40 has a first imaging element 60 and a second imaging element 62. Between the first imaging element 60 and the second imaging element 62, an intermediate image 63 is generated in an intermediate image plane 64. A chromatic graduated filter is inserted in the intermediate image plane 64. The chromatic graduated filter 65 can have long-pass, short-pass or bandpass filter properties. If a long-pass filter behavior is present, for example, then the wavelength of the filter edge varies with the impingement position of the measurement radiation on the chromatic graduated filter 65. The choice of the chromatic graduation is dependent on the structure of the illumination pattern 46. By way of example, if a structure of concentric rings as illustrated in FIG. 3 is used, then the chromatic graduated filter also has a concentric graduation. The wavelength of the filter edge then decreases or increases from the center of the chromatic graduated filter toward the edge. In the case of a linear-grating-type transmission structure 42, for example, the filter edge would increase or decrease from one edge of the chromatic graduated filter 65 to the other. Instead of the chromatic graduated filter, it is also possible to use a diffractive optical element in order to obtain a comparable function. All the remaining properties of the exemplary embodiments of FIG. 6 substantially correspond to the exemplary embodiments in FIG. 1. In the embodiment in FIG. 6, however, the beam splitter 34 is preferably a polarization-splitting beam splitter in order to avoid a complex superordinate spectral splitting.

FIG. 7 shows yet another embodiment of the measuring device 10. In this case, the transmission structure 42 is embodied in such a way that a grid-shaped arrangement of points arises as illumination pattern 46, wherein a light source of the illumination device 14 is embodied in a spectrally wide-band fashion. The front optical element 36 and the transverse optical element 38 likewise have large longitudinal chromatic aberrations. A hole pattern arrangement or a pinhole array 66 is provided in a confocal plane of the imaging system to the optical sensor arrangement 18. A multi-line spectrometer is provided as the optical sensor arrangement 18. The pinhole array is a diaphragm having holes arranged in grid form, wherein the holes correspond laterally to the illumination points. As it were a multi-point diaphragm is thus present. The multi-line spectrometer can be realized here for example by an areal camera being equipped with the aid of prisms, gratings or diffractive optical elements such that each line of the camera forms a line spectrometer. Provision can be made for each hole of the pinhole array 66 to be optically connected to a corresponding line of the line spectrometer by means of an optical waveguide 68, for example an optical fiber. In this way, a parallelized chromatic confocal sensor arises Alternatively, the transmission structure 42 in FIG. 7 can also be designed as a transmission slit. In this case, a confocal slit diaphragm would be inserted in the confocal plane upstream of the optical sensor arrangement 18. The confocal slit diaphragm is then imaged onto the entrance slit of the multi-line spectrometer. A linearly parallelized chromatic confocal sensor is thereby obtained, without optical waveguides 68 having to be used.

FIG. 8 shows yet another embodiment of the measuring device 10. Identical elements are once again identified by identical reference signs and will not be explained again. The illustration in FIG. 8 shows a so-called hybrid sensor unit. The construction using the front optical element 36 corresponds, in principle, to that of the previous exemplary embodiments. Instead of a transverse optical element 38, however, an autonomous additional sensor unit is present. For this purpose, a further illumination device 70, a further sensor arrangement 72, a further optics, optics 74 that is telecentric, in particular on the measurement object side, and a further pattern generating device 76 are provided. In this way, a further beam path 80 arises, along which a further illumination pattern 46 can be projected onto the measurement object 12 perpendicular to an illumination beam path 24 or at any other angle desired. At least one beam deflecting element 78 is provided for this purpose. A beam deflecting element 78 brings about an expansion of the further beam path 80 at least via a circumferential arc section 82. In principle, the beam can be expanded to a complete circumferential arc. Under certain circumstances, a circumferential arc section, in particular of 180°, is also sufficient. This prevents the measuring device 10 having to be rotated in order to avoid collisions with the surface of a measurement object 12, for example of a drilled hole.

The optical sensor arrangement 18 and/or the further optical sensor arrangement 72 can be connected to an evaluation device 84 for evaluating the images detected by the optical sensor arrangement 18 and/or the further optical sensor arrangement 72. The connection can be embodied as wire-based, but also wireless.

Particularly in the case of a configuration of the housing 20 having a housing section 22 extending in elongate fashion, the further beam path 80 can be guided outside the housing section extending in elongate fashion. By way of example, a diameter or the shape of drilled holes or other depressions can thus be determined by means the further beam path 80. The beam path through the front optical element 36 can in this case primarily fulfill the task of measuring the depth of a drilled hole and/or avoiding a collision of the measuring device 10 with the end of the drilled hole.

FIG. 9 illustrates an embodiment of an apparatus 100 comprising the measuring device 10. The apparatus 100 can be a coordinate-measuring machine, for example. The coordinate-measuring machine 100 has a carrying structure 94, which for example carries the evaluation device 84 and can move a sensor head 92 in three dimensions, said sensor head having the measuring device 10.

In principle, provision can be made for the transmission structure 42 to be configured as exchangeable, as is indicated by an arrow 86. In this way, different transmission structures can be specifically chosen in a usable manner.

As is illustrated in FIG. 10, it is possible to use for example transmission structures which do not have an illumination pattern 46 over the whole area. By way of example, a free central region 96 can be provided, such that normal image recording is effected in the free central region 96 of the illumination pattern 46. This is achieved by virtue of the fact that, for example, a central region 98 of the transmission structure 42 has no structuring whatsoever and allows an illumination radiation to pass through undeflected.

What is achieved in this way is that there is a modularity in the measuring device 10. In an apparatus 100, the measuring device 10 can be configured in an exchangeable manner as a traditional sensor unit such as a traditional tactile measuring head or a traditional optical probe head. A change of the transmission structure 42 can be used to flexibly adapt the sensor unit to the properties of a measurement object 12 to be measured. If the transmission structure 42 is completely removed, for example the embodiment in FIG. 9 can be used as a normal camera arrangement with two viewing directions.

A further configuration can provide for providing the pattern generating device 42, 36, 38 in combination with the illumination device 14 in the form of an LC display (liquid crystal display) or DMD (digital mirror device).

Using a transmission structure as in FIG. 10, the distance measurement outlined above can be effected in combination with a normal image recording by means of the free central regions 96.

Further combination possibilities can consist in using a part of the relay optics 32 for a supplementary optical measurement, for example an OCT measurement or a stray light measurement. Stray light measurements can be used, in particular, in order directly also to obtain roughness information about the surface besides the topological information. In this case, a further beam splitter can also be provided within the relay optics 32 in order to couple in the corresponding measurement beam paths.

A separating location 90 can be provided between the optical sensor arrangement 18 and the beam splitter 28 in order to couple, if appropriate, different embodiments with regard to illumination device and optics to the optical sensor arrangement 18. A separating location 88 can be provided on the measurement object side of the beam splitter 28, such that it is possible to provide different relay optical units 32 and deflections in the region of the beam splitter 34 with different front optical elements 36 and transverse optical elements 38. Different beam deflections 78 can also be exchanged in this way. By way of example, an adaptation to different measurement regions and diameters of bores can be effected in this way.

FIG. 11 illustrates a schematic flow chart of a method 110.

The method begins in a start step 112.

A first step 114 involves illuminating the measurement object 12 with an illumination pattern 46 having a positionally variant intensity distribution, wherein the illumination pattern 46 furthermore has a positionally and/or spectrally variant vertex focal length on the measurement object side. A step 116 involves detecting the illumination pattern reflected and/or scattered by the measurement object 12 by means of the optical sensor arrangement 18.

A step 118 then involves evaluating an image sharpness and/or a spectral distribution, in particular a spectral intensity distribution, over the entire detected illumination pattern 46, in particular detected by means of the optical sensor arrangement 18. In the context of the evaluation, an image evaluation can also be carried out so as to identify collisions rapidly and reliably, for example if a detected distance at the surface of the measurement object 12 continuously decreases. In this way, in particular, a prior warning or early identification of a collision can take place or an application as a proximity sensor can be implemented.

The method then ends in a stop step 120.

What is claimed is:

1. A measuring device for measuring a measurement object, comprising an illumination device for illuminating via illumination optics defining an illumination beam path the measurement object with an illumination pattern, a pattern generation device with at least one pattern generating element within the illumination beam path for bringing about a positionally variant intensity distribution of the illumination pattern, and an optical sensor arrangement for detecting via measurement optics defining a measurement beam path, the illumination pattern reflected and/or scattered by the measurement object, wherein the measurement beam path runs through at least part of said illumination optics, wherein the measuring device furthermore has optics which are telecentric at least on the measurement object side and which are arranged in the illumination beam path from the illumination device to the measurement object, wherein the optical sensor arrangement is further arranged in such a way that it detects the illumination pattern through at least one part of the telecentric optics, and wherein the pattern generating device with the at least one pattern generating element is designed in such a way that the illumination pattern has a positionally and/or spectrally variant vertex focal length distribution on the measurement object side.

2. The measuring device according to claim 1, wherein the optical sensor arrangement is a camera, and wherein the pattern generating device with the at least one pattern generating element is designed in such a way that the illumination pattern has a positionally variant vertex focal length distribution on the measurement object side.

3. The measuring device according to claim 1, wherein the optical sensor arrangement is a spectrometer or a spectrally resolving two-dimensional sensor, and wherein the pattern generating device with the at least one pattern generating element is designed in such a way that the illumination pattern has a spectrally variant vertex focal length distribution on the measurement object side.

4. The measuring device according to claim 1, wherein a pattern generating element of the pattern generating device is a transmission structure extending at least partly obliquely with respect to the beam path.

5. The measuring device according to claim 1, wherein a first pattern generating element of the pattern generating device is a planar transmission structure extending perpendicular to the beam path, and wherein a second pattern generating element of the pattern generating device is a refractive optical element having a longitudinal chromatic aberration or an optical element having a spherical aberration.

6. The measuring device according to claim 1, wherein the optics furthermore has a first beam splitter, which splits the beam path into a first measurement beam path and into a second measurement beam path, wherein the first measurement beam path and the second measurement beam path are oriented perpendicular to one another.

7. The measuring device according to claim 6, wherein the first beam splitter is a dichroic beam splitter.

8. The measuring device according to claim 6, wherein the first beam splitter is a polarization-optical beam splitter.

9. The measuring device according to claim 5, wherein the second pattern generating element of the pattern generating device is a refractive optical element having a longitudinal chromatic aberration, wherein the optics is designed in such a way that an intermediate image is generated in the optics, and wherein a chromatic graduated filter is arranged in a plane of the intermediate image.

10. The measuring device according to claim 1, wherein the illumination pattern generated by the pattern generating device is a grid-shaped point pattern, wherein a hole pattern arrangement is arranged between the optics and the optical sensor arrangement, wherein each hole of the hole pattern arrangement is connected to the optical sensor arrangement by means of an optical waveguide.

11. The measuring device according to claim 10, wherein the optical sensor arrangement is a multi-line spectrometer.

12. The measuring device according to claim 1, wherein the measuring device has a housing having a housing section extending in elongate fashion, wherein the optics has a relay optics in the housing section extending in elongate fashion, and wherein the beam path from the illumination device to the measurement object and a detection beam path from the measurement object to the optical sensor arrangement run parallel to one another through the relay optics.

13. A measuring device for measuring a measurement object, comprising an illumination device for illuminating the measurement object with an illumination pattern, a pattern generation device with at least one pattern generating element for bringing about a positionally variant intensity distribution of the illumination pattern, and an optical sensor arrangement for detecting the illumination pattern reflected and/or scattered by the measurement object, wherein the measuring device furthermore has an optics which is telecentric at least on the measurement object side and which is arranged in a beam path from the illumination device to the measurement object, wherein the optical sensor arrangement is arranged in such a way that it detects the illumination pattern through at least one part of the telecentric optics, and wherein the pattern generating device with the at least one pattern generating element is designed in such a way that the illumination pattern has a positionally and/or spectrally variant vertex focal length distribution on the measurement object side, and further wherein the measuring device furthermore has a further illumination device for illuminating the measurement object with a further illumination pattern, a further pattern generating device with at least one pattern generating element for bringing about a positionally variant intensity distribution of the further illumination pattern, a further optics which is telecentric at least on the measurement object side and which is arranged in a further beam path from the further illumination device to the measurement object, and a further optical sensor arrangement for detecting the illumination pattern reflected and/or scattered by the measurement object, wherein the further optical sensor arrangement is arranged in such a way that it detects the illumination pattern through at least one part of the further telecentric optics, and wherein the further pattern generating device with the at least one pattern generating element is designed in such a way that the further illumination pattern has a positionally and/or spectrally variant vertex focal length distribution on the measurement object side, and wherein the further optics has at least one beam deflecting element for expanding the further beam path via at least one circumferential arc section perpendicular to the beam path to the measurement object.

14. An apparatus for measuring a measurement object comprising a measuring device for measuring a measurement object, comprising an illumination device for illuminating via illumination optics defining an illumination beam path the measurement object with an illumination pattern, a pattern generation device with at least one pattern generating element within the illumination beam path for bringing about a positionally variant intensity distribution of the illumination pattern, and an optical sensor arrangement for detecting via measurement optics defining a measurement beam path, the illumination pattern reflected and/or scattered by the measurement object, wherein the measurement beam path runs through at least part of said illumination optics, wherein the measuring device furthermore has optics which are telecentric at least on the measurement object side and which is arranged in the illumination beam path from the illumination device to the measurement object, wherein the optical sensor arrangement is further arranged in such a way that it detects the illumination pattern through at least one part of the telecentric optics, wherein the pattern generating device with the at least one pattern generating element is designed in such a way that the illumination pattern has a positionally and/or spectrally variant vertex focal length distribution on the measurement object side, and wherein the apparatus furthermore has at least one evaluation unit for evaluating an image detected by means of the optical sensor arrangement.

15. An apparatus for measuring a measurement object comprising a measuring device for measuring a measurement object, comprising an illumination device for illuminating the measurement object with an illumination pattern, a pattern generation device with at least one pattern generating element for bringing about a positionally variant intensity distribution of the illumination pattern, and an optical sensor arrangement for detecting the illumination pattern reflected and/or scattered by the measurement object, wherein the measuring device furthermore has an optics which is telecentric at least on the measurement object side and which is arranged in a beam path from the illumination device to the measurement object, wherein the optical sensor arrangement is arranged in such a way that it detects the illumination pattern through at least one part of the telecentric optics, wherein the pattern generating device with the at least one pattern generating element is designed in such a way that the illumination pattern has a positionally and/or spectrally variant vertex focal length distribution on the measurement object side, wherein the measuring device furthermore has a further illumination device for illuminating the measurement object with a further illumination pattern, a further pattern generating device with at least one pattern generating element for bringing about a positionally variant intensity distribution of the further illumination pattern, a further optics which is telecentric at least on the measurement object side and which is arranged in a further beam path from the further illumination device to the measurement object, and a further optical sensor arrangement for detecting the illumination pattern reflected and/or scattered by the measurement object, wherein the further optical sensor arrangement is arranged in such a way that it detects the illumination pattern through at least one part of the further telecentric optics, and wherein the further pattern generating device with the at least one pattern generating element is designed in such a way that the further illumination pattern has a positionally and/or spectrally variant vertex focal length distribution on the measurement object side, and wherein the further optics has at least one beam deflecting element for expanding the further beam path via at least one circumferential arc section perpendicular to the beam path to the measurement object, and wherein the apparatus furthermore has at least one evaluation unit for evaluating an image detected by means of the optical sensor arrangement and/or the further optical sensor arrangement.

* * * * *